United States Patent [19]

Shaw et al.

[11] Patent Number: 5,891,696

[45] Date of Patent: Apr. 6, 1999

[54] COMPOSITIONS FOR CYTOCHROME P450 BIOTRANSFORMATION REACTIONS

[75] Inventors: Peter M. Shaw, Madison; Robert G. Lowery, Brooklyn; David V. Thompson, Monona, all of Wis.

[73] Assignee: Panvera Corporation, Madison, Wis.

[21] Appl. No.: 904,376

[22] Filed: Aug. 1, 1997

[51] Int. Cl.$^6$ .................................................. C12N 9/02
[52] U.S. Cl. ................................................................ 435/189
[58] Field of Search .............................................. 435/189

[56] References Cited

PUBLICATIONS

Eberhart, Delmont C. et al., "Cytochrome P450 IIIA1 (P450p) Requires Cytochrome b$_5$ and Phospholipid with Unsaturated Fatty Acids." *Archives of Biochemistry and Biophysics* 1991; 291; No. 2; 231–240.

Gillam, Elizabeth M. J. et al., "Expression of Modified Human Cytochrome P450 3A4 in *Escherichia coli* and Purification and Reconstitution of the Enzyme." *Archives of Biochemistry and Biophysics* 1993; 305; No. 1; 123–131.

Gillam, Elizabeth M. J. et al., "Expression of Cytochrome P450 3A5 in *Escherichia coli*: Effects of 5' Modification, Purification, Spectral Characterization, Reconstruction Conditions, and Catalytic Activities." *Archives of Biochemistry and Biophysics* 1995; 317; No. 2; 374–384.

Gorski, J. Christopher et al., "Regioselective Biotransformation of Midazolam by Members of the Human Cytochrome P450 3A (CYP3A) Subfamily." *Biochemical Pharmacology* 1994; 47; No. 9; 1643–1653.

Guengerich, F. Peter et al., "Characterization of Rat and Human Liver Microsomal Cytochrome P–450 Forms Involved in Nifedipine Oxidation, a Prototype for Genetic Polymorphism in Oxidative Drug Metabolism." *The Journal of Biological Chemistry* 1986; 261; No. 11; 5051–5060.

Holmans, Priscilla L. et al., "The High–Level Expression in *Eschericha coli* of the Membrane–Bound Form of Human and Rat Cytochrome b$_5$ and Studies on Their Mechanism of Function." *Archives of Biochemistry and Biophysics* 1994; 312; No. 2; 554–565.

Imaoka, Susumu et al., "Role of Phospholipids in Reconstituted Cytochrome P450 3A Form and Mechanism of Their Activation of Catalytic Activity." *Biochemistry* 1992; 31; 6063–6069.

Ingelman–Sundberg, Magnus et al., "High Rates of Substrate Hydroxylation by Human Cytochrome P450 3A4 in Reconstituted Membranous Vesicles: Influence of Membrane Charge." *Biochemical and Biophysical Research Communications* 1996; 221; 318–322.

Lee, Caroline A. et al., "CYP3A4 Expressed by Insect Cells Infected with a Recombinant Baculovirus Containing Both CYP3A4 and Human NADPH–Cytochrome P450 Reductase Is Catalytically Similar to Human Liver Microsomal CYP3A4." *Archives of Biochemistry and Biophysics* 1995; 319; No. 1; 157–167.

Muller–Enoch, Dieter et al., "Interaction of Liver Microsomal Cytochrome P–450 and NADPH–Cytochrome P–450 Reductase in the Presence and Absence of Lipid." *The Journal of Biological Chemistry* 1984; 259; No. 13; 8174–8182.

Nash, T., "The Colorimetric Estimation of Formaldehyde by Means of the Hantzsch Reaction." *Air Hygiene Laboratory, Public Health Laboratory Service* 1953; 55; 416–421.

Nelson, David R. et al., "P450 Superfamily: Update on New Sequences, Gene Mapping, Accession Numbers Nomenclature." *Pharmacogenetics* 1996; 6; 1–42.

Parkinson, Andrew, "Biotransformation of Xenobiotics,", (date N.A.).

Penman, B.W. et al., "Characterization of a Human Cell Line Expressing High Levels of cDNA–derived CYP2D6." *Pharmacogenetics* 1993; 3; 28–39.

Shaw, Peter M. et al., "Purification and Characterization of an Anticonvulsant–Induced Human Cytochrome P–450 Catalysing Cyclosporin Metabolism." *Biochem. J.* 1989; 263; 653–663.

Shaw, Peter M. et al., "Reconstitution Premixes for Assays Using Purified Recombinant Human Cytochrome P450, NADPH–Cytochrome P450 Reductase, and Cytochrome b$_5$–" *Archives of Biochemistry and Biophysics* 1997; 348; No. 1; 107–115.

Shen, Anna L. et al., "Structural Analysis of the FMN Binding Domain of NADPH–Cytochrome P–450 Oxidoreductase by Site–directed Mutagenesis." *J. Biological Chemistry* 1989; 264; No. 13; 7584–7589.

Shephard, Elizabeth A. et al., "Quantification of Cytochrome P450 Reductase Gene Expression in Human Tissues." *Archives of Biochemistry and Biophysics* 1992; 294; No. 1; 168–172.

Ueng, Yune–Fang et al., "Cooperativity in Oxidations Catalyzed by Cytochrome P450 3A4." *Biochemistry* 1997; 36; 370–381.

Werringloer, Jurgen, "Assay of Formaldehyde Generated During Microsomal Oxidation Reactions." *Microsomal Electron Transport and Cyt P–450* 297–302 (date N.A.).

Yamazaki, Hiroshi et al., "Roles of Divalent Metal Ions in Oxidations Catalyzed by Recombinant Cytochrome P450 3A4 and Replacement of NADPH–Cytochrome P450 Reductase with Other Flavoproteins, Ferredoxin, and Oxygen Surrogates." *Biochemistry* 1995; 34; 8380–8389.

*Primary Examiner*—Keith D. Hendricks
*Attorney, Agent, or Firm*—Mark K. Johnson

[57] ABSTRACT

A storable biotransformation mixture that can oxidize a drug, comprising a cytochrome P450 enzyme, an electron donor; and, a buffer solution. In a preferred embodiment the mixture also contains liposomes, cytochrome b$_5$ and NADPH-P450 reductase as the electron donor. The mixture is storable at a temperature less than 8° C. to for at least two weeks and is able to oxidize a drug after storage.

22 Claims, 13 Drawing Sheets

A

B

COMPOSITIONS FOR CYTOCHROME P450 BIOTRANSFORMATION REACTIONS

This application is a continuation of provisional application Ser. No. 60/023,073, filed Aug. 2, 1996.

FIELD

The field of the invention relates to biotransformation reactions and cytochrome P450. More particularly, it involves the generation of protein/lipid compositions containing a cytochrome P450 enzyme for performing biotransformation reactions.

BACKGROUND OF THE INVENTION

A mammalian liver contains enzymes that convert various chemical compositions to products which can be more easily eliminated from the body. This conversion process, which is also known as chemical metabolism or chemical biotransformation, frequently determines the duration of action of pharmaceuticals or the intensity of the pharmaceutical action. For this reason, many pharmaceuticals must typically be taken several times each day to treat diseases and produce other desirable pharmacological effects.

The liver includes many pharmaceutical-metabolizing enzyme systems such as cytochrome P450, carboxylesterases, UDP-glucuronosyltransferases, sulfotransferases, glutathione S-transferases and many others. These enzyme systems contain numerous individual enzymes, each of which is capable of metabolizing a wide variety of pharmaceuticals and other chemical compositions. Of these various enzyme systems, the P450 enzymes play a major role in determining the rate of elimination of drugs.

Cytochrome P450 enzymes comprise a large family of proteins (Nelson et al 1996) generally called isozymes or isoenzymes. Other new members of this family are still being discovered. In fact, relatively few species have been examined to this date, but, it is expected that the total number of enzymes will eventually be determined to be quite large. Current molecular biological techniques allow the generation of mutants of existing P450 enzymes and the construction of fusion proteins containing parts of P450 enzymes. These generated or constructed proteins still retain P450 function and as such are considered P450 proteins herein. Although liver cells (hepatocytes) contain the most cytochrome P450, other extrahepatic tissues also express other important isozymes, for example adrenals. The primary site for cytochrome P450 isozymes in hepatocytes is the endoplasmic reticulum.

Cytochrome P450 catalytic activity is considered a biotransformation reaction because substrates are changed in some way by the action of the enzyme. Three examples include introduction of a hydroxyl or epoxide functional group and dealkykation. In most cases of P450 biotransformation a source of electrons and molecular oxygen is required. Although hydroperoxides can substitute for both oxygen and electrons, in in vitro systems.

Without cytochrome P450 and related enzymes, naturally occurring and man-made foreign chemicals would accumulate in the body. However, biological or toxic effects of some chemicals are due to metabolites generated by cytochrome P450 and/or related enzymes. For example, the pharmacological effects of the anti-histamine, Seldane, are not due to its main ingredient, terfenadine, but are instead due to a metabolite of terfenadine that is generated by cytochrome P450. Similarly, the liver toxicity that can result from taking acetaminophen, the active ingredient in tylenol, is not due to acetaminophen per se, but is due to a toxic metabolite that is generated by cytochrome P450.

Metabolism by cytochrome P450 often represents the rate-limiting step in pharmaceutical elimination. Consequently, factors that lessen the activity of P450 enzymes usually prolong the effects of pharmaceuticals, whereas factors that increase cytochrome P450 activity have the opposite effect.

Changes in pharmaceutical metabolism may have undesirable or toxic consequences. For example, impaired metabolism of a pharmaceutical by factors that decrease cytochrome P450 activity may lead to symptoms of pharmaceutical overdose. In particular, the anti-coagulant warfarin can cause bleeding disorders when administered to individuals with low cytochrome P450 activity. Since the ulcer treatment drug cimetidine depresses P450 activity, warfarin is not administered to patients on cimetidine. Conversely, the accelerated metabolism of a drug due to increased concentrations of cytochrome P450 can also lead to a lessening of therapeutic effect. For example, pharmaceuticals such as phenobarbital and rifampin that increase cytochrome P450 activity lead to an increased rate of metabolism of contraceptive steroids. When the contraceptive steroids are consumed ovulation, and pregnancy, can result.

The liver converts many chemicals other than pharmaceuticals to metabolites that can be more readily eliminated from the body. Cytochrome P450 and related enzymes facilitate the elimination of endobiotics and of foreign chemicals called xenobiotics. To perform this function in their native environments, other components are often required such as other proteins, lipids, oxygen and electrons. Xenobiotics include environmental pollutants, pesticides, industrial chemicals, household products, cosmetics and non-nutrients in food such as plant alkaloids, flavorings, and chemicals that form during spoilage or cooking. Endobiotics are chemicals made in the body, such as steroid hormones, ecosanoids, and fat-soluble vitamins.

Cytochrome P450 biotransformation of different substrates including endogenous molecules and drugs can have a profound effect on the pharmacological and toxicological responses observed in different species. Because of this fact, pharmaceutical companies spend a considerable amount of their research time identifying the role of drug metabolizing enzymes, in particular cytochrome P450 enzymes, in the metabolism and disposition of novel therapeutics.

The need to determine if an enzyme or enzymes metabolize a drug is long standing. Information on P450 enzymes metabolizing a drug can be used to predict a variety of drug reactions. When administered with ketoconazole or erythromycin, the anti-histamine Seldane (active ingredient, terfenadine) causes Torsades de Points, which in some individuals leads to ventricular arrhythmias and heart failure. Terfenadine is extensively metabolized by intestinal and hepatic enzymes. When enzymes are inhibited by ketoconazole or erythromycin, the plasma levels of terfenadine become sufficiently elevated to block cardiac potassium channels. Such blockage may cause fatal ventricular arrhythmias.

Different sources have been used to measure P450 biotransformation reactions such as whole animals, tissue samples, cell fractions, and highly purified P450s. For example:

i) Radiolabelled drugs such as erythromycin and caffeine can be administered to human patients and P450 biotransformation capacity estimated from the amount of radiolabelled $CO_2$ exhaled. Drugs are administered to humans and biotransformed by P450 enzymes and the rate of biotransformation determined by measuring parent drug or metabolite concentrations in urine or plasma samples.

ii) Some techniques require the use of whole organ perfusions, tissue slices and cultured cells.

iii) Microsomes, a crude biochemical preparation in which membrane fragments of the endoplasmic reticulum have been selectively enriched from other components of the cell, are prepared from a variety of tissues and are then used as a common source of material. More unrefined techniques use crude cell fractions such as a "S9" fraction.

iv) Recombinant P450s may be generated in a variety of different heterologous expression systems, e.g. insect cells, yeast, E. coli. These eukaryotic and bacterial cells are used to over-express P450s and drug metabolizing enzymes. The cells are then used in a similar fashion as described in ii–iii.

v) Highly purified P450 isozymes have been isolated from both human tissue samples and from heterologous expression systems, however, the P450 does not perform biotransformation reactions alone. The functional biotransformation activity of the P450 has to be reconstituted. In the simplest reconstitution scenario a P450 isozyme is mixed with a substrate and a hydroperoxide chemical (which serves as an electron donor) only then can biotransformation occur.

Traditionally, reconstitution of P450 biotransformation activity has been more complex and has involved the addition of several other components. For example a typical reconstitution reaction might consist of a purified P450, another protein termed P450 reductase (which supplies electrons to the P450) a lipid component, a substrate and an electron source such as NADPH.

Another example indicates how complex some biotransformation reconstitution reactions can be. Using a purified cytochrome P450 which possesses optimal activity toward a substrate testosterone named CYP3A4, three highly purified lipids were pretreated to form a liposomes complex. The liposome complex was then mixed with the purified P450, P450 reductase and another protein cytochrome $b_5$. Other components at predetermined concentrations such as CHAPS, $MgCl_2$, GSH, were also required for optimal biotransformation capacity. Most importantly, the way in which all the components were combined was critical for obtaining useable biotransformation capacity. For example, mixing the protein and lipids was the first step and other components for optimal catalytic activity were added at specific points in time. Multiple variations of this reconstitution technique exist in the literature including different ratios of catalytic enzymes, P450 enzymes, lipids, detergent, buffer components, sonicated lipids, nonsonicated lipids, separation of vesicles containing proteins from unincorporated proteins and proteins mixed at high concentrations in the absence of lipid.

Accordingly, it is desirable to provide a method for simplifying the identification of particular drugs and chemicals which are metabolized by a cytochrome P450 enzyme for use in preventing or modifying the administration of the drug to individuals having abnormal concentrations of the enzymes which metabolize the drug.

SUMMARY

In a preferred embodiment, we have developed a storable biotransformation mixture that can oxidize a drug when utilized, comprising a cytochrome P450 enzyme, an electron donor; and, a buffer solution. In another preferred embodiment the mitre also contains liposomes, cytochrome $b_5$ and NADPH-P450 reductase as the electron donor. The mixture is storable at a temperature less than 8° C. to for at least two weeks and is able to oxidize a drug after storage.

We have developed a composition which, in another preferred embodiment, predetermined protein and lipid components and other chemicals are combined using stringent requirements and then frozen. The frozen solution can then be thawed out at one's convenience and cytochrome P450 reconstitution assays performed far more rapidly and efficiently than previous assays. This composition avoids the complicated and time consuming process that has been a necessity in the past.

In another preferred embodiment, the protein compositions contain a combination of liposomes and three recombinant human proteins: cytochrome P450 3A4 (P450), NADPH-P450 reductase, cytochrome $b_5$. The buffer composition contains reagents which, when diluted, provide for optimal metabolic activity with selected P450 3A4 substrates.

We have demonstrated the preparation of P450 compositions from recombinant proteins that retain functional activity when stored frozen for extended periods of time. In addition, the P450 3A4 compositions can undergo multiple freeze/thaw cycles without loss in biotransformation capacity. Turnover numbers of P450 3A4 substrates by the compositions were similar to that reported previously for reconstitution reactions performed with purified P450. The development of this stable reconstituted format provides several advantages to performing biotransformation assays with purified recombinant proteins:

i) it overcomes the perceived difficulties associated with performing P450 reconstitution reactions;

ii) the error in biotransformation activity is lowered due to a significant decrease in pipetting manipulations;

iii) the ratio of the individual purified enzyme components can easily be optimized to suit specific experimental requirements;

iv) the results demonstrate the feasibility of making similar compositions for other P450 enzymes;

v) a system is provided where catalysis by other drug metabolizing enzymes is prevented allowing for the rapid identification of novel P450 substrates and inhibitors and the development of large scale screening assays.

Reference is now made in detail to the preferred embodiments of the invention, examples of which are illustrated n the accompanying drawings.

DETAILED DESCRIPTION OF THE INVENTION

Figure 1:
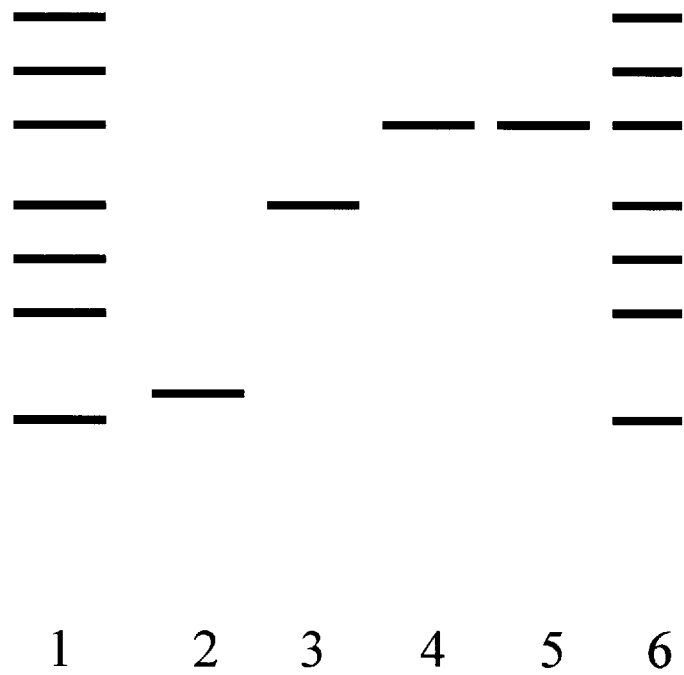
FIG. 1 shows sodium dodecyl sulfate-polyacrylamide gel electrophoresis analysis of purified proteins.

Since cytochrome P450 can metabolized a wide range of chemicals and/or related enzymes or other enzymes, the term drug is used herein as defining any chemical, endogenous or foreign, that is metabolized by cytochrome P450 and/or related enzymes or other bodily enzymes.

The development of enzyme and buffer compositions for in vitro biotransformation assays is described. The protein compositions contain a mixture of liposomes and three recombinant human proteins, cytochrome P450 (P450) 3A4, NADPH-P450 reductase, cytochrome $b_5$. The buffer composition contains reagents which, when diluted, provide for optimal metabolic activity with selected P450 3A4 substrates. P450 3A4 compositions were competent in the oxidation of known substrates including testosterone, midazolam, nifedipine, erythromycin, benzphetamine, and amitriptyline. Compositions stored at −80° C. for two months and those that underwent an additional five freeze/thaw cycles were able to hydroxylate testosterone at turnover rates similar to freshly prepared reconstitution mixes. In addition, compositions stored unfrozen at 4° C. for two weeks showed no significant loss in the rate of testosterone 6β-hydroxylation by P450 3A4. Compositions prepared with and without reduced glutathione, a component which had previously been found to be important for P450 3A4 reactions, were efficient at carrying out testosterone hydroxylation under these conditions. Kinetic parameters determined for the metabolism of testosterone, amitriptyline, nifedipine, and benzphetamine, using compositions were compared with human pooled microsomes and insect microsomes prepared from cells infected with a baculovirus containing two cDNA inserts coding for P450 3A4 and NADPH-P450 reductase. Each format gave different $V_{max}$ and $K_m$ values indicating different catalytic efficiencies. The availability of human P450 recombinant enzymes and the development of the P450 compositions that remain active after being stored frozen should allow for rapid identification of novel P450 substrates and inhibitors and the development of large scale screening assays.

Cytochrome P450 (P450 and/or CYP) enzymes comprise a large family of enzymes involved in the oxidative biotransformation of a wide variety of organic molecules which include endogenous, as well as xenobiotic compounds e.g. steroids, ecosanoids, aromatic hydrocarbons, pesticides, and drugs. In the liver, P450 enzymes are located in the endoplasmic reticulum of hepatocytes along with NADPH-P450 reductase, which donates electrons for catalysis, and cytochrome $b_5$, which can modulate P450 catalysis in vitro, apparently with or without electron transfer in various situations.

Currently, P450 enzymes representing five gene families are known to be expressed to some extent in human adult liver: CYP1A2, CYP2A6, CYP2B6, CYP2C8, CYP2C9, CYP2C18, CYP2C19, CYP2D6, CYP2E1, CYP3A4, CYP3A5, CYP4A9, CYP4A11, and CYP7. Both genetic and environmental factors play a role in the types of allelic variants and levels of individual enzymes observed in different human (ethnic) populations and individuals within these groups. It has been well documented that the type and levels of these hepatic isozymes expressed by an individual can have a major impact on the detoxification of xenobiotics, the activation of carcinogens, and the metabolism of a wide variety of pharmacologically important drugs. Members of the CYP3A subfamily, which represent approximately 30% and sometimes as much as 60% of the total expressed P450 in adult human liver, are known to be involved in the metabolism of numerous compounds including, erythromycin, nifedipine, testosterone, cyclosporine, lidocaine, imipramine, quinidine, midazolam, verapamil, troleandomycin, and terfenadine (1, 2).

One approach we have used to better understand and characterize the molecular interactions and substrate specificity of CYP3A members is by purification of the native and, more recently, the bacterially-expressed recombinant isozymes. Substrate specificity of the purified enzymes is determined by reconstitution of enzyme activity. In vitro reconstitution assays require combining multiple components including purified P450, NADPH-P450 reductase, lipids that have been sonicated to make liposomes, detergent, and buffer additives. Many techniques have been developed that use different methods to combine the components to form a functional enzyme complex, which is then used for biotransformation assays. Reconstitution of P450 3A4 appears to be more complex than for other P450s. For example, reasonable turnovers for a variety of CYP2E1 and CYP1A2 substrates can be achieved in reconstitution systems containing a single lipid, L-α-dilauroyl-sn-glycero-3-phophocholine. However, optimal activity for P450 3A4 substrates such as testosterone and nifedipine, but not others such as erythromycin and benzphetamine, is affected by the composition of the liposomes, the concentration of divalent cations, the presence of GSH, the buffer type, and the ratio of the other protein components.

The reconstitution process is tedious, time consuming, and prone to error. This is due, in part, to the multiple pipetting required for each of the various stages (combining all the components for reconstitution, preincubations for complex formation, and the subsequent biotransformation reactions) and because classically all these stages needed to be performed on the same day, due to lack of information on stability of the protein components. Historically, microsomal P450s were never frozen in the absence of glycerol or other polyols because of early evidence showing the protective action of these agents. In early work, a protective effect of GSH was reported, and thiols are often used with P450s.

In an effort to make the whole process simpler and more amenable for researchers, we have abandoned the traditional methodology and describe here the development of novel P450 3A4 compositions that can be stored and used conveniently when they are thawed. The advantage of these compositions is that they overcome both the perception and technical barriers associated with performing large numbers of P450 assays using purified components in a reliable fashion.

EXAMPLE 1

Materials And Methods

Protein expression and purification. Plasmids containing modified cDNAs encoding P450 3A4 and human cytochrome $b_5$ were transformed into *Escherichia coli* and grown in liquid expression medium. Cells were harvested and recombinant human and rat proteins were purified with minor modification of established procedures for P450 3A4, and human cytochrome $b_5$. Human NADPH-P450 reductase was purified from insect microsomes infected with a baculovirus that contained a human cDNA clone, as previously described. Rat reductase was purified from *E. coli*. (for procedures, see: Shaw, P. M., Barnes, T. S., Cameron, D., Engeset, J., Melvin, W. T., Omar, G., Petrie, J. C., Rush, W. R., Snyder, C. P., Whiting, P. H., Wolf, C. R., and Burke, M. D. (1989) *Biochem. J.* 263, 653–663; Holmans, P. L., Shet, M. S., Martin-Wixtrom, C. A., Fisher, C. W., and Estabrook, R. E. (1994) *Arch. Biochem. Biophys.* 312, 554–565; Shephard, E. A., Palmer, C. N. A., Segall, H. J., and Phillips, I. (1992) *Arch. Biochem. Biophys.* 294, 168–172; Shen, A. L., Porter, T. D., Wilson, T. E., and Kasper, C. B. (1989) *J. Biol. Chem.* 264, 7584–7589 incorporated herein by reference.)

EXAMPLE 2

Reconstitution and biotransformation assays

Simplified Composition system: a batch of the 5× P450 3A4 protein composition (0.5 µM P450 3A4, 1.0 µM NADPH-P450 reductase, 0.5 µM cytochrome $b_5$, 0.5 mg CHAPS/ml, 0.1 mg/ml liposomes [L-α-dilauroyl-sn-glycero-3-phosphocholine, L-α-diloleoyl-snglycero-3-phosphocholine, L-α-dilauroyl-sn-glycero-3-phosphoserine (1:1:1, w/w/w per ml)], 3.0 mM GSH and 50 mM potassium HEPES, pH 7.4) and a 5× buffer mix (200 mM potassium HEPES, pH 7.4, 12 mM GSH, and 150 mM $MgCl_2$) was prepared and frozen at −80° C. and −20° C. in 1.0 and 1.5 ml aliquots. The 5× protein compositions were made as follows. Liposomes were prepared in the absence of Ar (for procedure see Gillam, E. M. J., Guo, Z., Ueng, Y.-F., Hiroshi, H., Cock, I., Reilly, P. E. B., Hooper, W. D., and Guergerich, F. P. (1995) *Arch. Biochem. Biophys.* 317, 374–384; incorporated herein by reference). The purified proteins and liposomes were mixed together on ice; then HEPES, GSH, and CHAPS were added, with water used to adjust the components to the final concentration as described above.

A typical 300 µl biotransformation reaction was prepared by mixing, (on ice) 60 µl of 5×P450 3A4 protein composition and an equal volume of 5×buffer mix. $H_2O$ and substrate were then added to bring the reaction almost to the working 1×concentration. The subsequent addition of 6 µl of 100 mM NADPH caused the individual components to achieve the exact 1×concentration. Some experiments used a NADPH-generating system comprised of 0.5 mM NADP$^+$, 2 units of glucose 6-phosphate dehydrogenase/ml, and 10 mM glucose 6-phosphate. Unless otherwise stated (in other reactions where the final reaction volume was different), the concentration of the compositions remained as described above.

EXAMPLE 3

Fresh standard

The individual protein and buffer components were aliquoted from stock solutions into 1.5 ml microcentrifuge tubes to achieve approximately 2.5×solutions and incubated on ice for 10 min. $H_2O$ and substrate were added and the mixtures were preincubated at 37° C. for 3 min, followed by addition of NADPH to start the biotransformation reactions. The addition of substrate and NADPH adjusted the components to the same concentrations as for the simplified mixtures.

EXAMPLE 4

Analytical assays

The assay conditions varied depending on the substrate tested. Most of the assays were modified so that reactions could be performed in 1.5 ml microflige tubes.

In the testosterone 6β-hydroxylation assay, the final concentration of testosterone was 200 µM unless otherwise indicated. The reactions were stopped after 10 min at 37° C. by either, addition of 90 µl of 0.66 mM 11β-hydroxytestosterone, dissolved in a 2:1 mixture of $CH_3CN$ and $CH_3OH$ or with 0.5 volumes of a mixture of 1M $Na_2CO_3$ and 2M NaCl (pH 10.5). HPLC analysis of the products, after extraction with 1 ml of $CH_2Cl_2$, was performed as previously described (for procedure see Guengerich, F. P., Martin, M. V., Beaune, P. H., Kremers, P., Wolff, T., and Waxman D. J. (1986) *J. Biol. Chem.* 261, 5051–5060; incorporated herein by reference).

Midazolam 1- and 4-hydroxylation assays were performed as described previously (for procedure see Gorski, J. L., Hall, S. D., Jones, D. R., VandenBranden, M., and Wrighton S. A. (1994) *Biochem. Pharmacol.* 47, 1643–1653; incorporated herein by reference).

Nifedipine assays were performed as described previously.

Benzamphetamine N-demethylation was measured following the reaction in the presence of 1.0 mM d-benzphetamine. Reactions (0.5 ml) were quenched by the addition of 0.5 volume of a mixture of 1M $Na_2CO_3$ and 2M NaCl (pH 10.5), and extracted with 2 volumes of $CH_2Cl_2$. The contents of the tubes were mixed using a vortex device and the layers were separated by centrifugation (450×g for 10 min). An aliquot of the organic (lower) layer was transferred to a glass tube and dried under $N_2$. The residue was dissolved in 100 µl of column mobile phase and the substrate and product (N-benzylamphetamine) were separated on a Develosil ODS-HG-5 HPLC column using a mixture of 10 mM potassium phosphate, pH 4.0: $CH_3CN$ (35:65, v/v) containing 0.02% (v/v)$(C_2H5)_3$N. The flow rate was 1.5 ml per min and detection was at 254 nm.

Amitriptyline N-demethylation assays were done as described elsewhere (for procedure see Ueng, Y-F., Kuwabara, T., Chun, Y-J., and Guengrich, F. P. (1997) *Biochemistry* 31, 370–381; incorporated herein by reference).

Erythromycin metabolism was determined by measuring formaldehyde production, using the Nash procedure as previously described (for procedure see Nash, T. (1951) *Biochem. J.* 55, 416–421 Werringloer, J. (1978) *Methods Enzymol.* 52, 297–302; incorporated herein by reference).

Protein concentration was estimated using the bicinchoninic acid (BCA) assay (Pierce, Rockford, Ill.). P450 and cytochrome $b_5$ concentrations and NADPH-P450 reduction activity were measured as previously described (for procedure see Shaw, P. M., Barnes, T. S., Cameron, D., Engeset, J., Melvin, W. T., Omar, G., Petrie, J. C., Rush, W. R. Snyder, C. P., Whiting, P. H., Wolf, C. R., and Burke, M. D. (1989) *Biochem. J.* 263, 653–663; incorporated herein by reference) using extinction coefficients of 91 mM$^{-1}$ cm$^{-1}$($\Delta\epsilon_{450\text{-}490}$ for Fe$^{2+}$CO vs. Fe$^{2+}$), 100 mM$^-$cm$^{-1}$($\delta\epsilon_{425}$ for Fe$^{2+}$ vs. Fe$^{3+}$), and 21 mM$^{-1}$ cm$^{-1}$($\Delta\epsilon_{550}$ for reduced cytochrome c), respectively.

EXAMPLE 5

Reagents

Human pooled microsomes were purchased from XenoTech L.L.C. (Kansas City, Kans.). Midazolam and the 1- and 4-hydroxy metabolites were a kind gift from Hoffinan-La Roche (Nutley, N.J.). P450 3A4 Baculosomes™ were prepared at PanVera Corporation (Madison, Wis.). Briefly, *Trichoplusia ni* cells were infected with a baculovirus containing cDNA inserts for human CYP3A4 and rabbit NADPH-P450 reductase as previously described (for procedure see Lee, C. A., Kadwell, S. H., Kost, T. A., and Serabjit-Singh, C. J. (1995) *Arch. Biochem. Biophys.* 319, 157–167; incorporated herein by reference). The infected cells were harvested by centrifugation and microsomes prepared using a procedure descibed elsewhere (for procedure see Penman, B. W., Reece, J., Smith, T., Yang, C. S., Gelboin, H. V. Gonzalez, F. J., and Crespi, C. L. (1993) *Pharmacogenetics* 3, 28–39; incorporated herein by reference). All other reagents were obtained from commercial sources and were analytical grade or better.

EXAMPLE 6
Purification Results

We focused our initial studies on P450 3A4 because of its importance in drug metabolism and because reconstitution of this P450 is more complex than others. We reasoned that if we succeeded in developing a simplified system for P450 3A4, then other P450s could easily be substituted into a similar system.

The purification of the components used for reconstitution experiments followed standard, well-documented procedures and the purity of the proteins was >90% as demonstrated using sodium dodecyl sulfate-polyacrylamide gel electrophoresis as a criterion (FIG. 1). The specific content or activity of each of the three proteins, shown in Table I, was in agreement with previously published results.

In FIG. 1 each protein (2 $\mu$g) was loaded onto a 4–20% acrylamide pre-prepared gradient Novex gel (San Diego, Calif.) and electrophoresed under denaturing conditions according to the manufacturers instructions. From left to right, Lane 1 and 6; $M_r$ markers (150, 100, 75, 50, 35, 25, and 15, kDa), Lane 2; cytochrome $b_5$, Lane 3; P450 3A4 Lane 4; rat NADPH-P450 reductase, Lane 5; human NADPH-P450 reductase.

EXAMPLE 7
Stability

Our rationale for deciding how to design the protein compositions was defined by several criteria that had to be met to allow flexibility for P450 3A4 biotransformation reactions:

1) Different final concentrations of P450 needed to be achieved in the reaction mix, typically between 10–200 pmol P450 per ml, to accommodate the expected variation in turnover rates for different substrates.

2) Most P450 substrates are hydrophobic and have to be dissolved either in an organic solvent (which should make up <2% of the total reaction volume to prevent interference in oxidation reactions) or a relatively large amount of aqueous solution. Therefore, the buffer and protein compositions would preferably make up 50% or less of the total reaction volume.

3) As in item 2, sufficient volume should be left to allow for addition of NADPH or an NADPH-generating system and other components that might need to be added such as specific inhibitors of P450 metabolism.

Previous studies had shown that optimal P450 3A4 biotransformation reactions required the inclusion of 3 mM GSH and 30 mM $MgCl_2$. We therefore opted to make two compositions at a 5× concentration that would occupy 40% of the total reaction volume, leaving 60% for the addition of substrate and electron donor. The buffer composition contained the high concentrations of $MgCl_2$, GSH, and HEPES buffer that when diluted 5 fold, would give optimal component concentrations. Similarly, the 5× protein composition contained 0.5 $\mu$M P450 3A4 at a 1:2:1 molar ratio of P450 3A4 to NADPH-P450 reductase to cytochrome $b_5$. The ratio of the proteins was chosen based on previous experiments that had proven optimal for several P450 3A4 biotransformation reactions and the concentration of the P450 after dilution to 1× would be 100 nM.

Our first experiments were designed to determine if compositions that contained proteins and liposomes could remain functional after multiple freeze/thaw cycles. Compositions that had been frozen at −80° C. for at least two months, upon thawing, dilution, addition of substrate and NADPH (as described in Materials and Methods) were able to oxidize testosterone, a specific substrate for P450 3A4. The results (Table II) indicate that the turnover number for testosterone 6$\beta$-hydroxylation in the reconstituted systems prepared from stored compositions is very similar, if not slightly greater, than reconstitution mixes prepared on the same day. Importantly, the turnover number was not affected even when the compositions were subjected to five freeze/thaw cycles. Compositions were functionally stable for at least two months at −80° C. and could undergo multiple freeze/thaw cycles without a loss in catalytic activity. We also investigated the catalytic capacity of the P450 compositions stored at −20° C. and 4° C. The activity of the compositions toward testosterone remained relatively constant at both these temperatures for two weeks, as shown in FIGS. 2 and 3.

Figure 2:
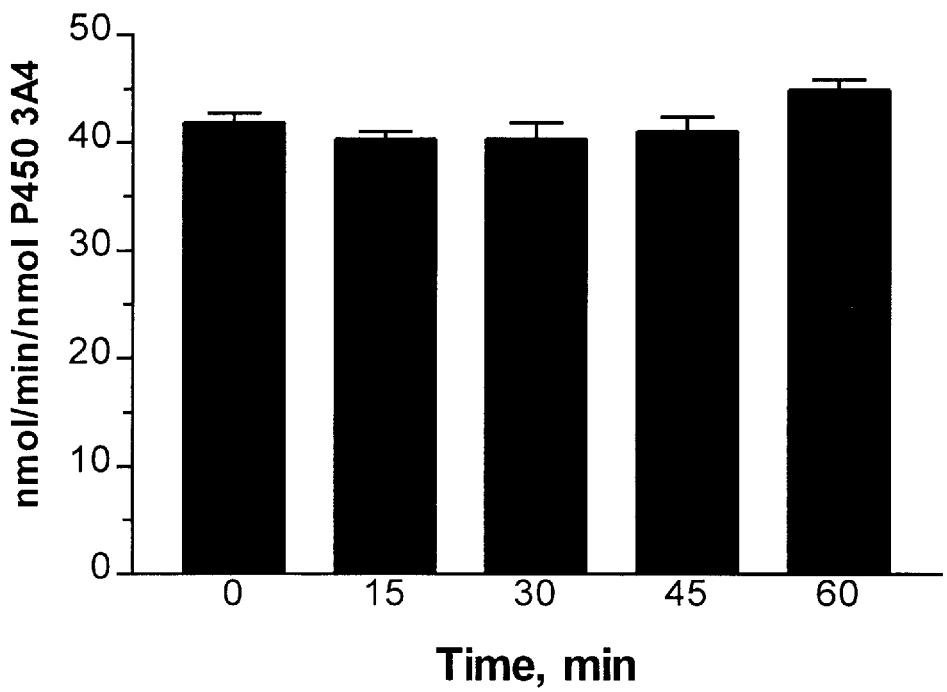
FIG. 2 is a plot showing stability of the compositions on ice for one hour.

In FIG. 2, a single set of 5×P450 3A4 protein and buffer compositions was thawed and diluted to almost 1× on ice as described in Materials and Methods. At the indicated times testosterone reactions were performed as described in the legend for Table II. The mean turnover number, with standard deviation, is shown for triplicate results at each time point. A statistical analysis (ANOVA) performed on the results indicated that the mean at 60 minutes is different from the means at the other time points (p<0.05).

Figure 3:
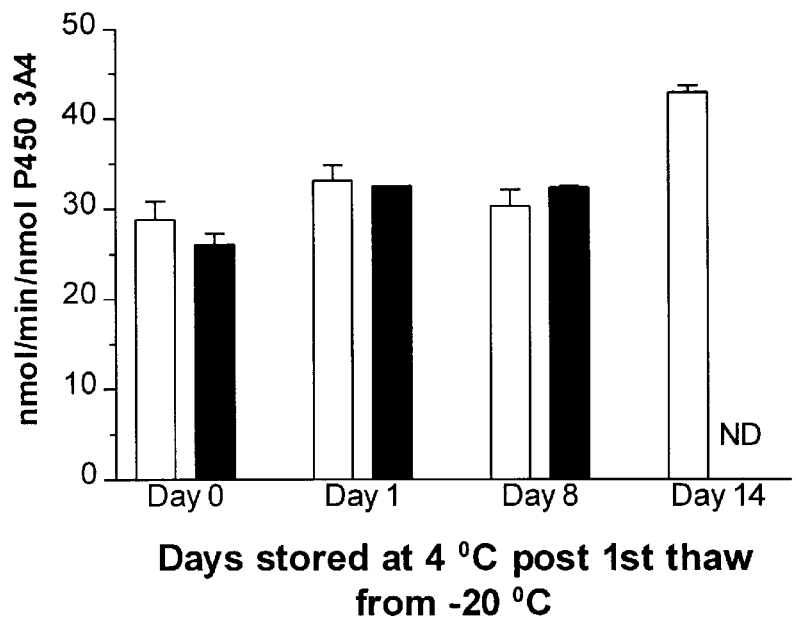
FIG. 3A is a bar graph showing stability of the compositions stored at 4° C. after −20° C. over a period of two weeks.
FIG. 3B is a bar graph showing stability of the compositions stored at −20° C. after −20° C. over a period of two weeks.
Figure 3:
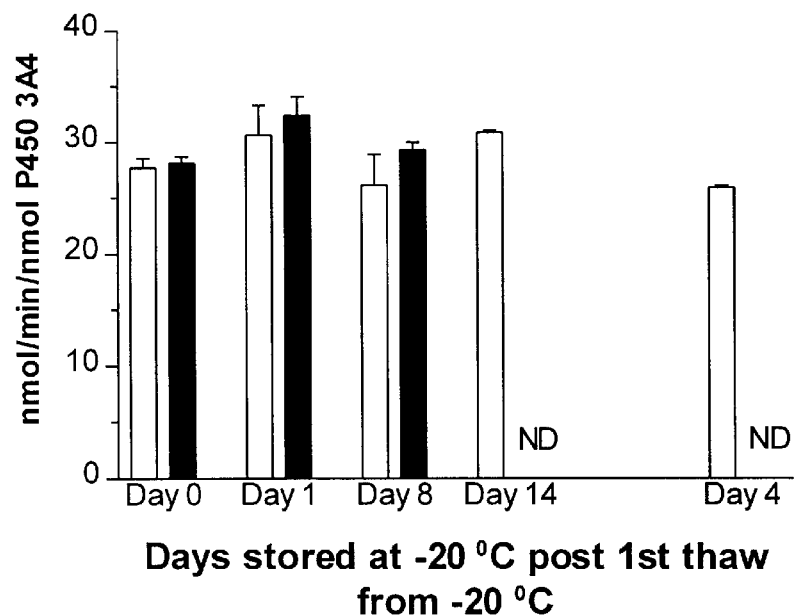
Figure 4A:
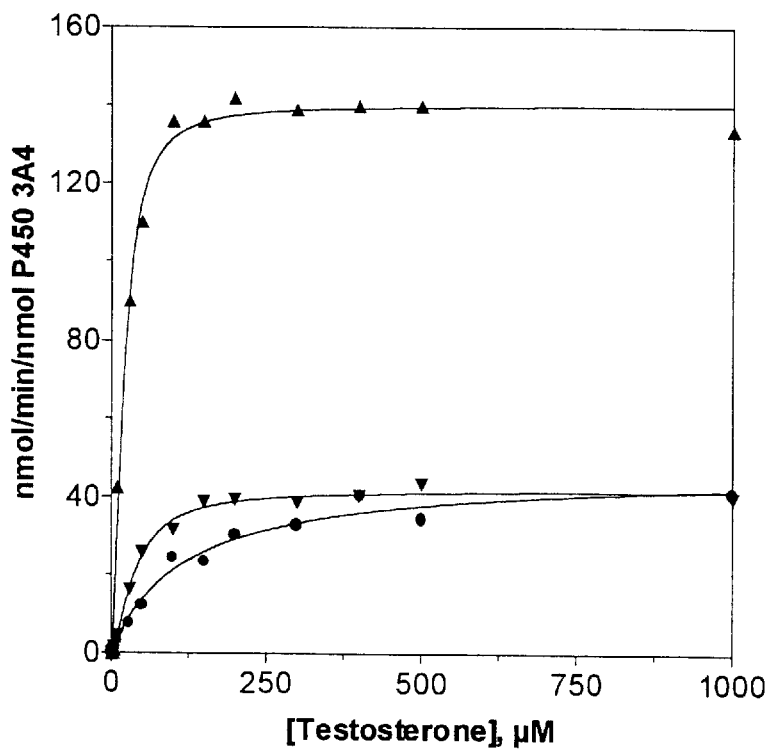
FIG. 4 is a graph showing determination of the kinetic parameters of testosterone, benzphetamine, amitriptyline, and nifedipine metabolism using different enzyme systems.
Figure 4B:
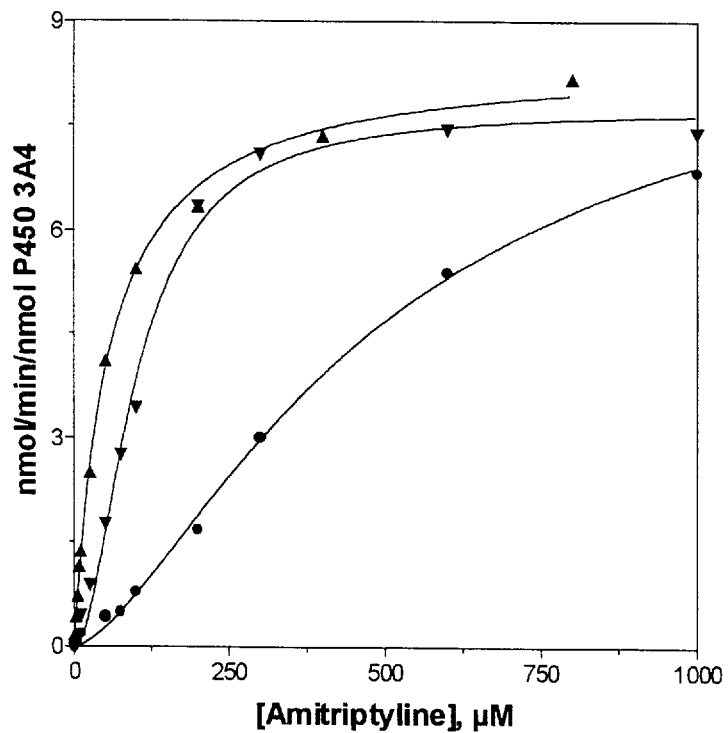
Figure 4C:
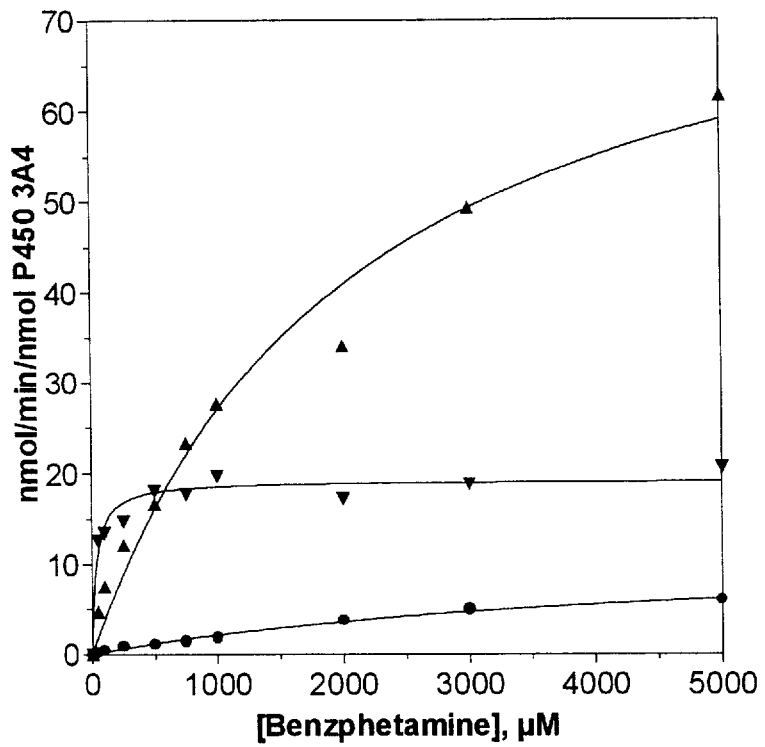
Figure 4D:
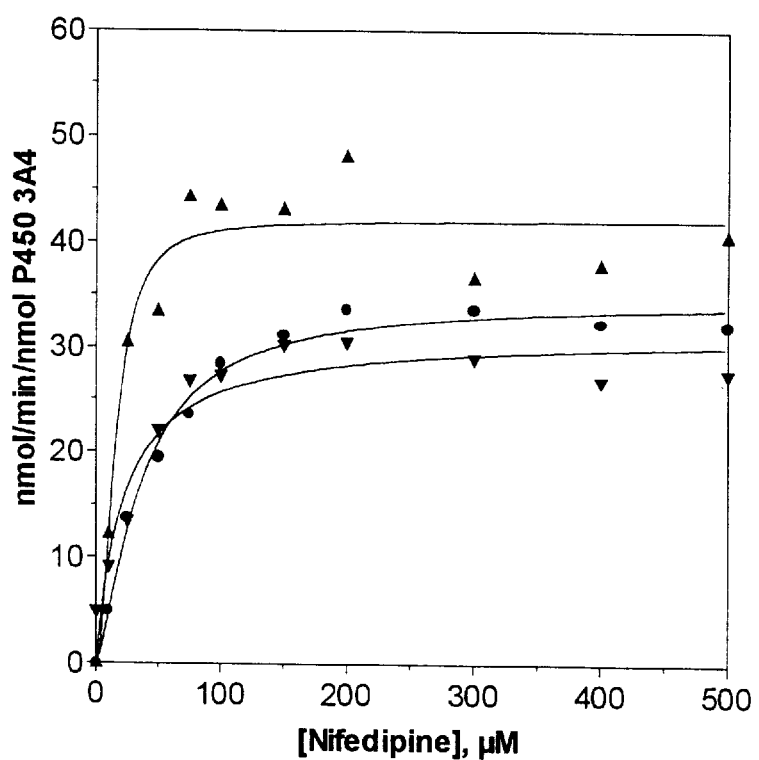

In FIG. 3, a single set of 5×P4503A4 protein and buffer compositions generated with (open bars) and without (shaded bars) GSH were thawed from −20° C. and used to measure testosterone 6$\beta$-hydroxylation activity (Day 0) as described in materials and methods. The samples were then stored at 4° C. or −20° C. and retested on the indicated days. Samples stored at −20° C. were thawed and refrozen on the day of testing.

In addition, the absence of GSH in the compositions had an insignificant affect on testosterone hydroxylation activity for the time period tested, one week. The results from the various stability tests at different temperatures demonstrated the feasibility of using compositions of P450 and associated electron transfer proteins for biotransformation reactions. These results also demonstrated that it was possible to make up large batches of compositions with recombinant proteins to generate a single batch of composition that could be used for multiple reactions, thus eliminating variation associated with making reconstitution mixes on a daily basis.

EXAMPLE 8
Reproducibility

To test the robustness of the P450 3A4 compositions, four individuals were asked to follow a protocol to measure testosterone hydroxylation. Each individual performed at least four assays from the same batch but different aliquots of the P450 3A4 protein and buffer compositions. The results (Table III) indicate that the greatest variation observed in measuring testosterone 6$\beta$-hydroxylation with the compositions was inter-individual. However, the coefficients of variation in six out of eight cases were <10 percent, indicating good reproducibility when any one individual performed the assay. Also, the difference in the mean activity obtained on day 1 and 2 was not significantly different, even when the samples from the individuals who have the largest coefficient of variation were eliminated from a Students t-test.

EXAMPLE 9

Biotransformation capability

We evaluated the potential of the simplified reconstituted system to oxidize several known P450 3A4 substrates (Table IV). The turnover numbers for the simplified reconstituted system are generally higher than those reported in the literature. However, the turnover numbers are very similar to the estimated turnover number for P450 3A4 in pooled human microsomes, based on the assumption that on the average about 30% of the total P450 is P450 3A4 and that other P450s do not participate in product formation.

We determined the kinetic parameters for the metabolism of testosterone, benzphetamine, nifedipine, and amitriptyline by human pooled microsomes, microsomes prepared from insect cells overexpressing both P450 3A4 and NADPH-P450 reductase, and in the simplified reconstituted system. The results for each enzyme system were analyzed using a non-linear regression plot (FIG. 4), which yielded estimates of $V_{max}$ and $K_m$ values (Table V).

In FIG. 4 reconstitution reactions were performed as described in materials and methods except that the protein composition was 2× to improve sensitivity for the benzphetamine and amitryptyline assays. Human microsomal assays were performed in 0.10M potassium phosphate buffer (pH 7.4) and at a protein concentration of 100 μg/ml for testosterone, 400 μg/ml for amitriptyline and nifedipine, and 200 μg/ml for benzphetamine. Insect cell microsome assays were performed as with human microsomes at protein concentrations of of 100 μg/ml for testosterone, 288 μg/ml for amitriptyline and benzphetamine, and 400 μg/ml for nifedipine. Each point represents duplicate determinations. The velocity for pooled human microsomes is calculated on the assumption that approximately 30% of the total P450 is P450 3A4 and that no other P450s contribute to product formation. Parts A, B C and D represent testosterone, amitriptyline, benzphetamine and nifedipine oxidations, respectively. Nifedipine and testosterone reactions were performed in the presence of 2 mM NADPH while benzphetamine and amitriptyline reactions were performed in the presence of an NADPH regenerating system, as described in materials and methods. Insect microsomes, (♦), human pooled microsomes, (♦) reconstituted reactions (●). The points were fit to non-linear regression curves using the computer program GraphPad PRISM (San Diego, Calif.). The data reflects the best fit (judged by the P value) according to a comparison of a Michaelis-Menten and sigmoidal equation. The equations used were: Michaelis-Menten, $v=(V_{max}S)/(K_m+S)$, and sigmoidal, $v=(V_{max}S^n)/(K_m^n+S^n)$.

The kinetic parameters for any one substrate were different in each of the P450 systems. The insect cell microsomes were observed to have the highest $V_{max}$ values in all cases. However, comparison of the three systems indicated that the differences in $V_{max}$ values were not as great for amitriptyline and nifedipine as they were for benzphetamine and testosterone; the $V_{max}$ values for pooled human microsomes and the compositions were within a factor of two.

The apparent $K_m$ values for the reconstituted system were higher than for the pooled microsomes although the differences in the $K_m$ values were dependent on the substrate examined. The insect microsomes were observed to have the lowest apparent $K_m$ values for testosterone, nifedipine, and amitriptyline but not benzphetamine. Interestingly, sigmoidal profiles, suggestive of cooperativity, were observed in some instances (indicated with Hill coefficients in table 5). The differences in the kinetic parameters in each system for any one substrate may result, in part, from differences in electron transfer capacity to the P450. This may not be surprising when one considers the different physical environments in which the P450 is located and also the estimated ratio of NADPH-P450 reductase to P450 3A4 in each of the systems, approximately 2:1, 0.2:1 and 8:1 for the reconstituted, human pooled microsomes, and insect microsomes, respectively; the higher levels of NADPH-P450 reductase probably explain the larger $V_{max}$ values in baculosomes.

In addition, another factor that may affect the kinetic parameters via electron transfer capacity is the presence of cytochrome $b_5$. The stimulatory affect on P450 3A4 catalysis of selected substrates by cytochrome $b_5$ in the reconstituted system has clearly been demonstrated. The insect microsomes used in these experiments contain no measurable spectral cytochrome $b_5$, yet, as mentioned above, the $V_{max}$ is much higher than either the reconstituted system or human microsomes which both have cytochrome $b_5$.

Figure 5:
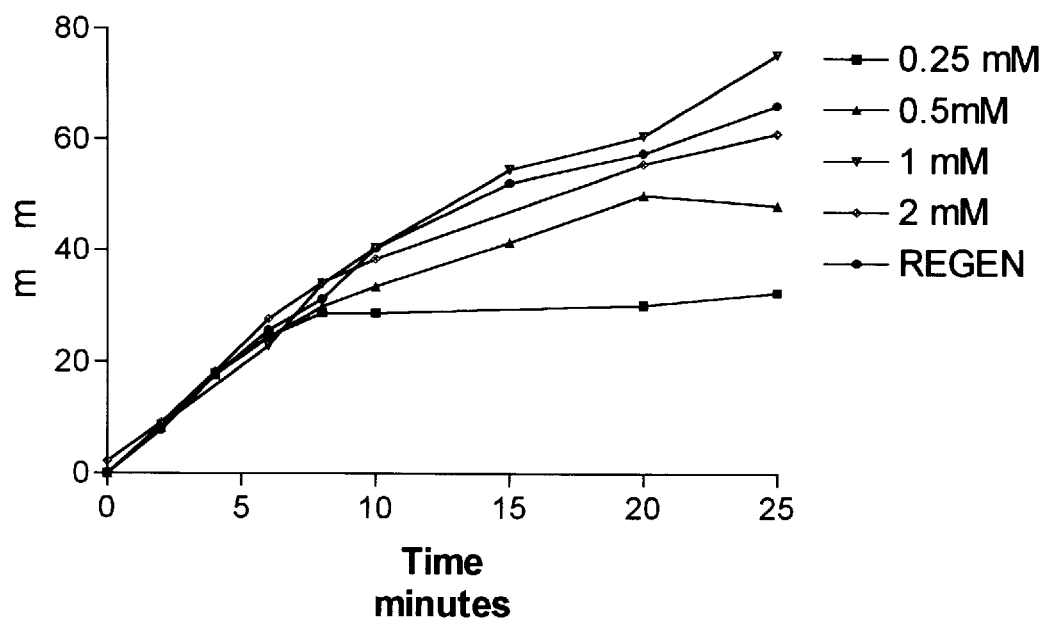
FIG. 5 illustrates the activity of CYP3A4 compositions with various NADPH concentrations and a regeneration system.

In FIG. 5, activity of CYP3A4 compositions generate activity with various NADPH concentrations and a regeneration system.

Figure 6:
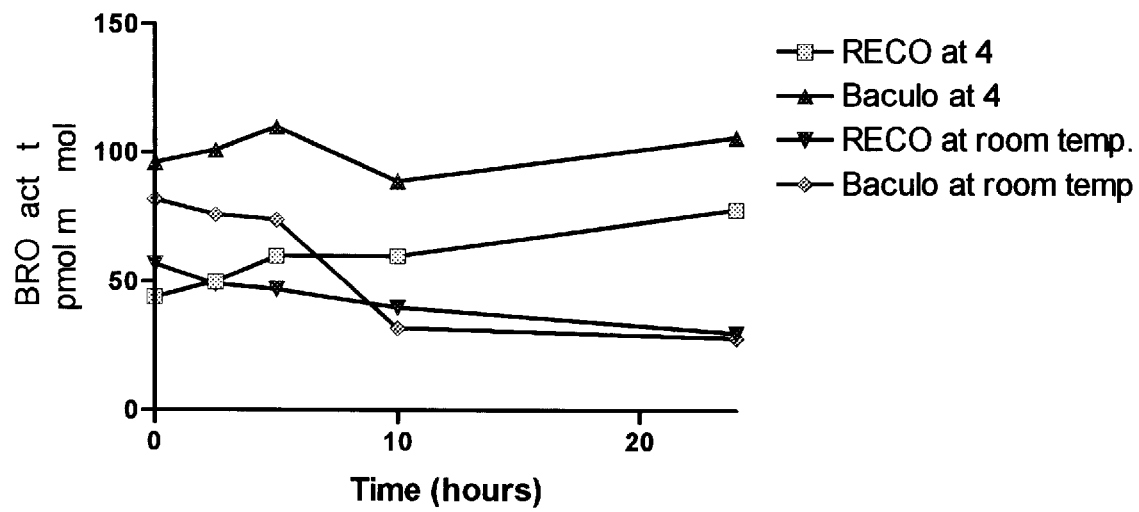
FIG. 6 shows the stability of the compositions at room temperature.

Referring to FIG. 6, baculosomes were diluted to 0.45 mg/ml in 0.1M Tris-HCl, pH 7.5, containing 0.1 mM EDTA and the CYP3A4 compositions was diluted to 1×. Benzyloxyresorufin was added to a final concentation of 5 μM and reactions were started by the addition of NADPH to a final concentration of 0.5 mM at the indicated time points.

Figure 7:
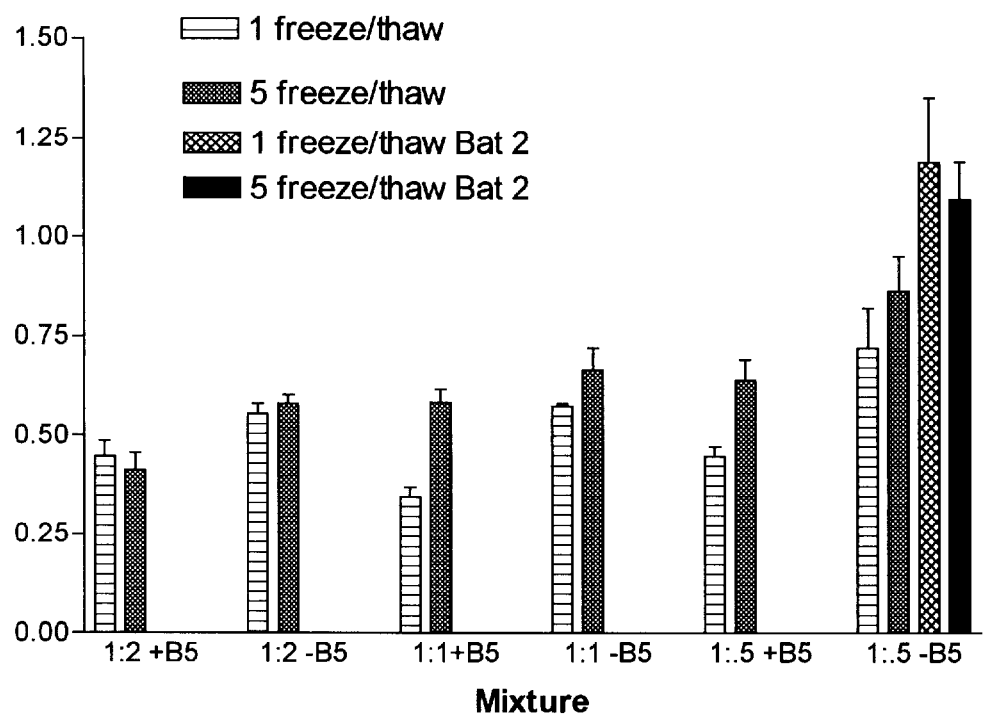
FIG. 7 is a bar graph illustrating the affect of freeze/thaw on the functional activity of the RECO CYP 1A2 with and without cytochrome $b_5$.

In reference to FIG. 7, CYP1A2 compositions were made exactly as CYP3A4 compositions in the presence and absence of cytochrome b5 and with the indicated reductase ratios. Reactions were performed using CYP1A2 composition at a P450 concentration of 25 pmol/ml, with 5 μM methoxyresorufin and 120 mM Na/K phospate buffer, pH 7.4. Addition of NADPH to 0.5 mM was used to start the reactions.

Figure 8:
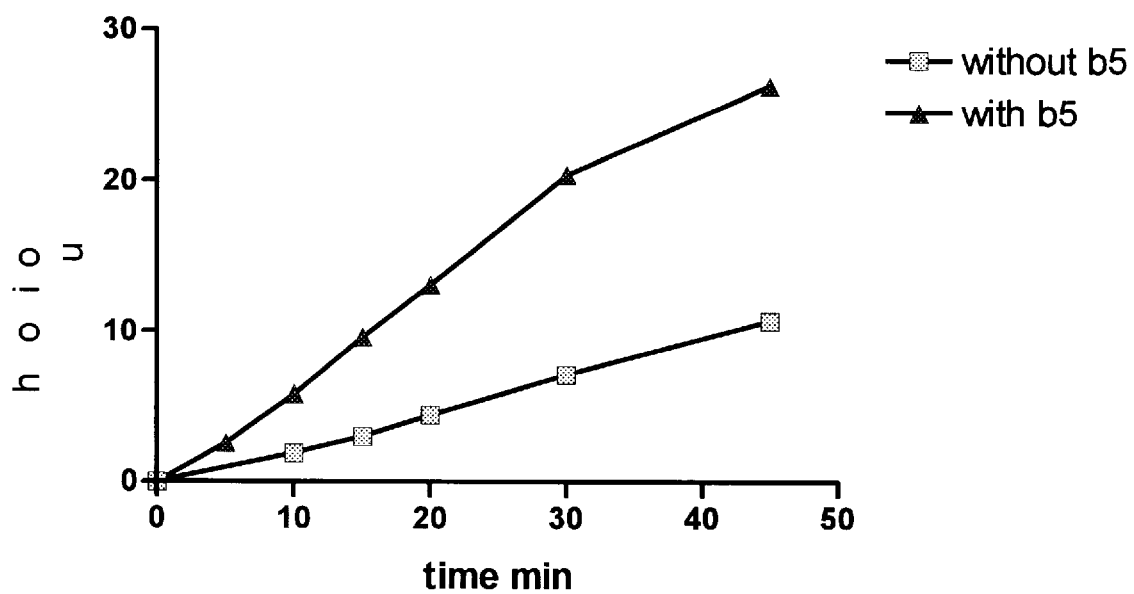
FIG. 8 indicates the time course of RECO 2C9 activity with and without cytochrome $b_5$.

As depicted in FIG. 8, CYP2C9 compositions were made exactly as CYP3A4 compositions in the presence and absence of cytochrome b5. Reactions were performed using CYP2C9 composition at a P450 concentration of 25 pmol/ml, with 100 μM diclofenac and 100 mM Tris-HCl, pH 7.5. Addition of NADPH to 2 mM was used to start the reactions.

Figure 9:
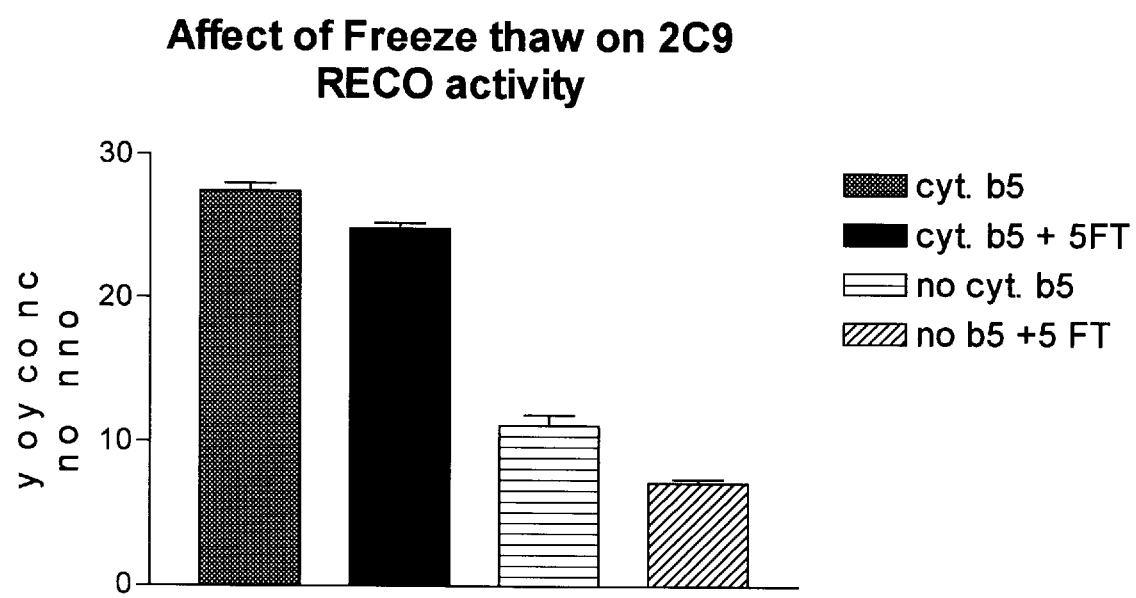
FIG. 9 is a bar graph showing the affect of freeze/thaw on the functional activity of the RECO 2C9.

In FIG. 9, reactions were performed as described in FIG. 8. Two different RECO formats are shown, those made in the presence of cyt. b5 and those made in the absence of cytochrome b5.

Figure 10:
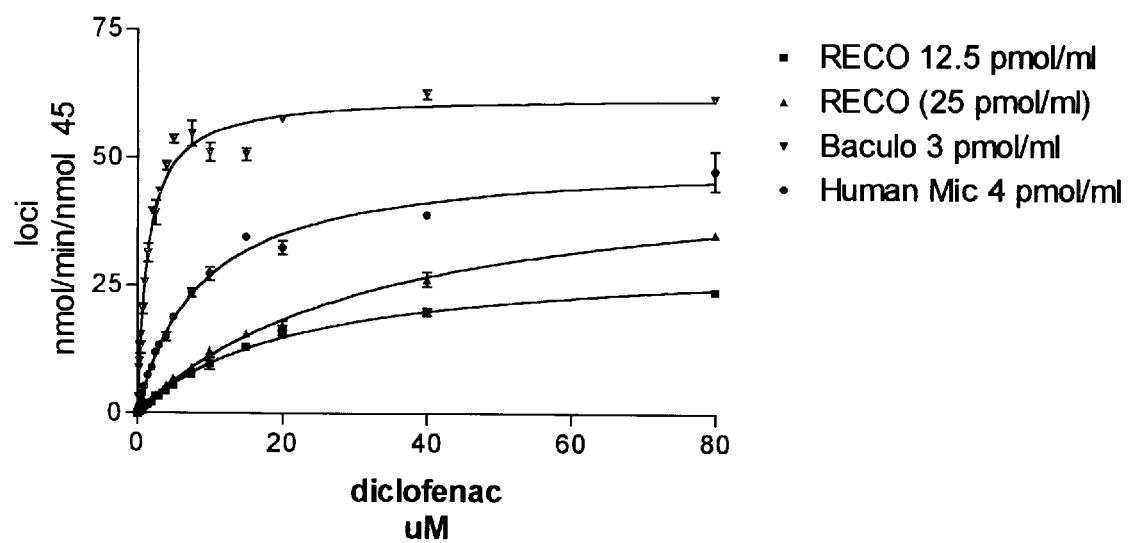
FIG. 10 is a plot showing determination of the kinetic parameters of diclofenac metabolism using different enzyme systems.

Pertaining to FIG. 10, reactions were performed as described in the legend to FIG. 4. The velocity for pooled human microsomes is calculated on the assumption that approximately 20% of the total P450 is P450 2C9 and that no other P450s contribute to product formation. Baculo=insect cell microsomes prepared at PanVera, RECO=the system we have developed, Human mic=human microsomes. Points were fit to non-linear regression curves using the computer program GraphPad PRISM (San Diego, Calif.).

TABLE I

Purified proteins used in reconstitution assays[a]

| Purified protein | Specific content or specific activity |
|---|---|
| P450 3A4 | 11 nmol/mg protein |
| Cytochrome $b_5$ | 60 nmol/mg protein |
| NADPH-P450 reductase (rat) | 55 μmol/min/mg protein |
| NADPH-P450 reductase (human) | 24 μmol/min/mg protein |

[a]Protein concentration, hemoprotein concentration, and NADPH-cytochrome c reduction activity were measured as described in materials and methods.

TABLE II

Stability of compositions after storage at −80° C.[a]

| Experiment 1 and 2 | Rate of 6β-hydroxytestosterone formation (nmol/min/nmol of CYP3A4) |
|---|---|
| Prepared on the same day | 26.0 ± 1.6 n = 5 |
| 2 months storage | 30.1 ± 0.4 n = 4 |
| 2 months storage + 5 freeze/thaws | 27.6 ± 3.3 n = 5 |
| Prepared on the same day | 26.8 ± 1.7 n = 5 |
| 2 months storage | 38.0 ± 2.5 n = 5 |
| 2 months storage + 5 freeze/thaws | 37.5 ± 4.3 n = 5 |

[a]The mean turnover number, standard deviation, and number of independent testosterone reactions performed from a standard reconstitution mix made on the day, and from a single set of 5X P450 3A4 protein and buffer compositions that had undergone a further 0 and 5 successive freeze/thaw cycles is shown. Reconstitution conditions were performed as described in materials and methods.

TABLE III

Reproducibility of P450 3A4 compositions[a]

Rate of testostosterone hydroxylation

| Day 1 | | Day 2 | |
|---|---|---|---|
| mean | rsd | mean | rsd |
| 44.4 ± 1.8 | 3.9 | 55.5 ± 3.4 | 6.2 |
| 42.8 ± 2.4 | 5.6 | 48.2 ± 1.0 | 2.2 |
| 38.6 ± 5.8 | 15.0 | 45.5 ± 6.6 | 14.4 |
| 50.0 ± 1.0 | 1.9 | 53.9 ± 1.7 | 3.1 |

[a]A single set of 5X P450 3A4 protein and buffer compositions was given to four individuals who performed testosterone hydroxylations as described in the materials and methods. The results show the mean turnover number (nmol/min/nmol of CYP3A4), standard deviation, coefficient of variation (relative standard deviation, rsd). The number of reactions performed by each individual were at least four.

TABLE IV

Turnover numbers of varios probe substrates using the P450 3A4 compositions.[a]

| Activity measured | Rate (nmol/min/nmol of CYP3A4) |
|---|---|
| Testosterone 6β-hydroxylation | 43.9 |
| Midazolam 1-hydroxylation | 9.0 |
| Midazolam 4-hydroxylation | 9.0 |
| Erythromycin N-demethylation | 8.8 |
| Benzphetamine N-demethylation | 4.8 |
| Nifedipine oxidation | 33.0 |

[a]Reconstitution reactions were performed as described in the materials and methods, except for N-demethylations, which were performed using a regenerating system and compositions that contained a 2X P450 3A4 protein composition. The final comcentration of each substrate was 200 μM testosterone, 200 μM nifedipine, 300 μM midazolam, 10 mM erythromycin, and 2 mM benzphetamine. The results ahown are average of at least duplicate reactions.

TABLE V

Kinetic Parameters[a]

| | Testosterone | | | | Amitriptyline | | | |
|---|---|---|---|---|---|---|---|---|
| P450 | $V_{max}$ | $K_m$ | $V_{max}/K_m$ | n | $V_{max}$ | $K_m$ | $V_{max}/K_m$ | n |
| Human microsomes | 46 ± 2 | 46 ± 8 | 1 | 1.6 ± 0.2 | 7.7 ± 0.3 | 100 ± 10 | 0.077 | 1.9 ± 0.2 |
| Reconstituted | 47 ± 2 | 120 ± 20 | 0.4 | n/a | 9.3 ± 1.0 | 490 ± 80 | 0.019 | 1.5 ± 0.1 |
| Baculosomes | 150 ± 10 | 25 ± 6 | 6 | 1.7 ± 0.2 | 8.5 ± 0.1 | 56 ± 3 | 0.15 | n/a |

| | Benzphetamine | | | | Nifedipine | | | |
|---|---|---|---|---|---|---|---|---|
| P450 | $V_{max}$ | $K_m$ | $V_{max}/K_m$ | n | $V_{max}$ | $K_m$ | $V_{max}/K_m$ | n |
| Human microsomes | 19 ± 1 | 35 ± 17 | 0.54 | n/a | 32 ± 2 | 23 ± 6 | 1.4 | n/a |
| Reconstituted | 12 ± 2 | 4400 ± 1300 | 0.0027 | n/a | 35 ± 1 | 37 ± 3 | 0.95 | 1.4 ± 3 |
| Baculosomes | 84 ± 13 | 2100 ± 700 | 0.040 | n/a | 45 ± 2 | 14 ± 4 | 3.2 | 2.0 ± 0.4 |

[a]The kinetic parameters were calculated from the fitted curves in FIG. 4 using the computer program GraphPad PRISM (San Diego CA.). $V_{max}$ values are in nmol/min/nmol of CYP3A4, $K_m$ values are in μM. The data reflects the best fit (judged by the P value) according to a comparison of a Michaelis-Menten and Sigmoidal equation. Where n/a is displayed, the best fit was to a Michaelis-Menten curve. In the cases of a best fit to a sigmoidal curve the Hill coeficient (n) was indicated. The equations used were: Michaelis-Menten, $v = (V_{max}S)/(K_m + S)$, and sigmoidal, $v = (V_{max}S^n)/(K_m^n + S^n)$ The foregoing is considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

We claim:

1. A biotransformation mixture that can be stored at a temperature less than 8° C. for at least two weeks and is able to oxidize a drug after storage, comprising:
   a) a cytochrome P450 enzyme;
   b) an electron donor;
   c) a lipid; and,
   d) a buffer solution.

2. The mixture of claim 1 further comprising cytochrome $b_5$.

3. The mixture of claim 1 wherein the lipid comprises a liposome.

4. The mixture of claim 1 wherein the electron donor comprises a reduced puridine dinucleotide.

5. The mixture of claim 4 wherein the reduced puridine dinucleotide comprises NADPH.

6. The mixture of claim 1 wherein the electron donor comprises a NADPH-P450 oxidoreductase, 7. The mixture of claim 6 wherein the electron donor comprises a human NADPH-P450 oxidoreductase selected from the group consisting of recombinant NADPH-450 and naturally occuring NADPH-P450.

8. The mixture of claim 1 wherein the cytochrome P450 is selected from the group consisting of: CYP1A2, CYP2A6, CYP2B6, CYP2C8, CYP2C9, CYP2C18, CYP2C19, CYP2D6, CYP2E1, CYP3A4, CYP3A5, CYP4A9, CYP4A11, and CYP7.

9. The mixture of claim 7 wherein the cytochrome P450 comprises a CYP1A2 enzyme.

10. The mixture of claim 7 wherein the cytochrome P450 comprises a CYP2C9 enzyme.

11. The mixture of claim 7 wherein the cytochrome P450 comprises a CYP3A4 enzyme.

12. The mixture of claim 7 wherein the human cytochrome P450 is selected from the group consisting of recombinant cytochrome P450 and naturally occurring cytochrome P450.

13. The mixture of claim 3 wherein the liposome is selected from the group consisting of: L-α-dilauroyl-sn-glycero-3-phosphocholine, L-α-diloleoyl-sn-glycero-3-phosphocholine, and L-α-dilauroyl-sn-glycero-3-phosphoserine.

14. The mixture of claim 1 wherein the buffer solution comprises sufficient amounts of $MgCl_2$ and GSH to allow the mixture to oxidize a drug.

15. The mixture of claim 1 wherein such mixture may be frozen at a temperature less than −20° C. for at least two months and is able to oxidize a drug upon thawing.

16. A biotransformation mixture that may be frozen at a temperature less than 0° C. and is able to oxidize a drug upon thawing, comprising:
   a) a cytochrome P450 enzyme;
   b) an electron donor;
   c) a lipid; and,
   d) a buffer solution.

17. The mixture of claim 16 wherein the cytochrome P450 is selected from the group consisting of: CYP1A2, CYP2A6, CYP2B6, CYP2C8, CYP2C9, CYP2C18, CYP2C19, CYP2D6, CYP2E1, CYP3A4, CYP3A5, CYP4A9, CYP4A11, and CYP7.

18. The mixture of claim 17 wherein the cytochrome P450 comprises a human enzyme selected from the group consisting of recombinant cytochrome P450 and naturally occurring cytochrome P450.

19. The mixture of claim 18 wherein the electron donor comprises NADPH.

20. The mixture of claim 18 wherein the electron donor comprises a NADPH-P450 oxidoreductase.

21. The mixture of claim 20 wherein the lipid comprises a liposome.

22. The mixture of claim 21 wherein the liposome is selected from the group consisting of: L-α-dilauroyl-sn-glycero-3-phosphocholine, L-α-diloleoyl-sn-glycero-3-phosphocholine, and L-α-dilauroyl-sn-glycero-3-phosphoserine.

* * * * *

UNITED STATES PATENT AND TRADEMARK OFFICE
CERTIFICATE OF CORRECTION

PATENT NO.   : 5,891,696  
DATED        : April 6, 1999  
INVENTOR(S)  : Shaw et al.

Page 1 of 1

It is certified that error appears in the above-identified patent and that said Letters Patent is hereby corrected as shown below:

<u>Title page,</u>
Insert Item
--            Related U.S. Application Data
[60]    Continuation of Provisional Application Serial No. 60/023,073, filed August 2, 1996. --.

Signed and Sealed this

Twenty-fifth Day of April, 2006

JON W. DUDAS
*Director of the United States Patent and Trademark Office*